(12) United States Patent
Su et al.

(10) Patent No.: US 7,445,335 B2
(45) Date of Patent: Nov. 4, 2008

(54) SEQUENTIAL WAVEFRONT SENSOR

(75) Inventors: Wei Su, Sunnyvale, CA (US); Yan Zhou, Pleasanton, CA (US); Qing Chun Zhao, Sunnyvale, CA (US)

(73) Assignee: Clarity Medical Systems, Inc., Pleasanton, CA (US)

( * ) Notice: Subject to any disclaimer, the term of this patent is extended or adjusted under 35 U.S.C. 154(b) by 160 days.

(21) Appl. No.: 11/335,980

(22) Filed: Jan. 20, 2006

(65) Prior Publication Data

US 2007/0171366 A1    Jul. 26, 2007

(51) Int. Cl.
*A61B 3/10* (2006.01)
(52) U.S. Cl. ............... 351/205; 351/200; 351/211; 250/201.9; 356/121
(58) Field of Classification Search ........... 351/200, 351/205, 206, 211; 600/489; 250/231.17, 250/201.9; 356/308, 121
See application file for complete search history.

(56) References Cited

U.S. PATENT DOCUMENTS

| | | | | |
|---|---|---|---|---|
| 4,141,652 | A | | 2/1979 | Feinleib |
| 5,164,578 | A | * | 11/1992 | Witthoft et al. .......... 250/201.9 |
| 5,568,208 | A | * | 10/1996 | Van de Velde ............. 351/221 |
| 5,777,719 | A | | 7/1998 | Williams et al. |
| 6,199,986 | B1 | * | 3/2001 | Williams et al. ............ 351/221 |
| 6,376,819 | B1 | | 4/2002 | Neal et al. |
| 6,685,317 | B2 | | 2/2004 | Su et al. |
| 6,791,696 | B1 | | 9/2004 | Fantone et al. |
| 6,964,480 | B2 | | 11/2005 | Levine |
| 2003/0053031 | A1 | * | 3/2003 | Wirth ...................... 351/221 |
| 2004/0004696 | A1 | * | 1/2004 | Davis et al. ................ 351/212 |
| 2005/0134851 | A1 | * | 6/2005 | Murphy et al. ............. 356/400 |

OTHER PUBLICATIONS

Liang, J. et al., "Objective measurement of wave aberrations of the human eye with the use of a Hartmann-Shack wave-front sensor," J. Opt. Soc Am. A. vol. 11, No. 7, Jul.

(Continued)

*Primary Examiner*—Ricky Mack
*Assistant Examiner*—James R Greece
(74) *Attorney, Agent, or Firm*—Charles E. Krueger

(57) ABSTRACT

A sequential wavefront sensor comprises a light beam scanning module, a sub-wavefront focusing lens, a detector with more than one photosensitive area and a processor for calculating the sequentially obtained centroids of a number focused light spots from the sub-wavefronts to determine the aberration of the input wavefront. A sequential wavefront sensing method comprises the steps of; sequentially projecting a number of sub-wavefronts onto a sub-wavefront focusing lens and a detector with more than one photosensitive areas, calculating the centroid of the focused light spot from each sub-wavefront, and processing the centroid information to determine the aberration of the wavefront. In particular, a method for auto-focusing and/or auto-astigmatism-correction comprises the steps of sequentially projecting a number of sub-wavefronts around an annular ring of a wavefront to a sub-wavefront focusing lens and a detector, calculating the centroid of focused light spot from each sub-wavefront to figure out the centroid trace and hence the defocus and/or astigmatism, adjusting the focus and/or astigmatism of the optical imaging system before the wavefront sensor so that the measured defocus and/or astigmatism is minimized.

36 Claims, 10 Drawing Sheets

OTHER PUBLICATIONS

Liang continued: 1994, pp. 1949-1957, copyright 1994 Optical Society of America.

Dave, T., "Wavefront aberrometry Part 1: Current theories and concept", Optometry Today, Nov. 19, 2004, pp. 41-45.

Ginis, H.S., et al., "Variability of wavefront aberration measurements in small pupil sizes using a clinical Shack-Hartmann aberrometer", BMC Ophthalmology, Feb. 11, 2004, 4:1, copyright 2004 Ginis et al.

* cited by examiner

SEQUENTIAL WAVEFRONT SENSOR

BACKGROUND OF THE INVENTION

Wavefront sensors are devices used to measure the shape of the wavefront of a light beam (see, for example, U.S. Pat. No. 4,141,652). In most cases, a wavefront sensor measures the departure of a wavefront from a reference wavefront or an ideal wavefront such as a plane wavefront. A wavefront sensor can be used for measuring both low order and high order aberrations of various optical imaging systems such as the human eye (see for example, J. Liang, et al. (1994) "Objective measurement of the wave aberrations of the human eye with the use of a Hartmann-Shack wave-front sensor," J. Opt. Soc. Am. A 11, 1949-1957; T. Dave (2004) "Wavefront aberrometry Part 1: Current theories and concepts" Optometry Today, Nov. 19, 2004 page 41-45). Furthermore, a wavefront sensor can also be used in adaptive optics in which the distorted wavefront can be measured and compensated in real time, using, for example, an optical wavefront compensation device such as a deformable mirror. As a result of such compensation, a sharp image can be obtained (see for example, U.S. Pat. No. 5,777,719).

Currently, most of wavefront sensors designed for measuring the aberration from human eye are Shack-Hartmann type, in which the measured wavefront is simultaneously divided in a parallel format into many sub-wavefronts. The essential components of such a sensor include a light source or input optical beam, an array of tiny lenses (called the lenslet array), and a camera or some other means for recording the pattern and location (also called centroid) of the spot images formed by the lenslets array.

FIG. 1 shows an exemplary prior art Shack-Hartmann sensor used for eye aberration measurement. An SLD (superluminescent diode) 102 is generally used as the light source and the light is delivered through the eye's optics (including the cornea 104 and the crystal lens 106) to a relatively small area on the retina 108. The scattered light from the retina 108 travels through the eye's optical imaging system (including the cornea 104 and the crystal lens 106) and emerge from the pupil as an aberrated wavefront 110. In order to suppress interference from light reflected by the cornea 104 and other optical interfaces such as those of the crystal lens 106 other than the retina 108, the input relatively narrow light beam is usually polarized by a first polarizer 112 in a first direction. Given that light scattered by the retina is much more depolarized, the retina scattered light is usually measured in a second orthogonal polarization direction with a second orthogonal analyzer 114.

One can use a relay optics system, for example, 116, consisting of a set of lenses, to magnify or de-magnify or simply transfer the aberrated wavefront onto a lenslet array 118. If the lenslet array 118 is in a pupil conjugate plane (an image plane of the pupil), the wavefront at the lenslet plane will be identical to or will be a magnified or demagnified version of the wavefront shape at the eye's pupil. The lenslet array 118 then forms an array of spot images on the CCD camera 120. If the eye is a perfect optical system, the wavefront at the lenslet array plane would be perfectly flat (as shown by the dashed straight line 122) and a uniformly distributed array of image spots would be recorded by the CCD camera 120 located at the focal plane of the lenslet array.

On the other hand, if the eye is not perfect, the wavefront 124 at the lenslet array will no longer be perfectly flat and will have irregular curved shapes. Consequently, the spot images on the CCD camera 120 will depart from the location corresponding to the aberration-free case. Through data processing of the image spot position on the CCD camera 120, both low order and high order aberrations of the eye can be determined (see for example, J. Liang, et al. (1994) "Objective measurement of the wave aberrations of the human eye with the use of a Hartmann-Shack wave-front sensor," J. Opt. Soc. Am. A 11, 1949-1957).

Although a wavefront sensor can measure both the low order and high order aberration of an optical imaging system, for a non-static imaging system such as the human eye, it has been shown that only low order aberrations corresponding to the sphero-cylindrical error measured from the central portion of the eye are relatively consistent (see for example, Ginis HS, et al. "Variability of wavefront aberration measurements in small pupil sizes using a clinical Shack-Hartmann aberrometer" BMC Ophthalmol. Feb. 11; 2004 4:1.).

In practice, for most eye aberration measurements and correction as well as for most fundus imaging optical systems, the optical aberrations that need to be measured and corrected are the sphero-cylindrical error (also called defocus and astigmatism). It is well known to those skilled in the art that these aberrations can be measured using a small number of sub-wavefronts around an annular ring of the input wavefront. In such a case, a large portion of the CCD detector arrays read out would be wasted. In order to save cost, a number of (typically 8 or 16) quad-detectors can be arranged around an annular ring of an aberrated wavefront to make the measurement of only these sub-wavefronts (see for example, U.S. Pat. No. 4,141,652, which, together with all other references cited, are herein incorporated in their entirety as references for this patent application).

However, with this arrangement, it is still necessary to use a multiple number of quad-detectors, which, although, are collectively less expensive than a large area CCD camera, but are still more costly than a single quad-detector. In addition, alignment a number of quad-detectors will also be much more difficult than that of a single quad-detector.

DETAILED DESCRIPTION OF THE INVENTION

Reference will now be made in detail to various embodiments of the invention. Examples of these embodiments are illustrated in the accompanying drawings. While the invention will be described in conjunction with these embodiments, it will be understood that it is not intended to limit the invention to any embodiment. On the contrary, it is intended to cover alternatives, modifications, and equivalents as may be included within the spirit and scope of the invention as defined by the appended claims. In the following description, numerous specific details are set forth in order to provide a thorough understanding of the various embodiments. However, the present invention may be practiced without some or all of these specific details. In other instances, well known process operations have not been described in detail in order not to unnecessarily obscure the present invention.

One embodiment of the present invention is a sequential wavefront sensor comprising a light beam scanning module, a sub-wavefront focusing lens, a detector with more than one photosensitive area and a processor for calculating the sequentially obtained centroids of the focused light spot from the sub-wavefronts to determine the aberration of the input wavefront. In this embodiment of the invention, the sub-wavefront focusing lens and the detector are fixed in space and an input beam is scanned by the light beam scanning module to sequentially project different portions of wavefront from input beam or a replica of the wavefront to the sub-wavefront focusing lens and the detector. The processor can be a computer or a programmable electronic board that can be used to calculate the centroid trace or pattern on a x-y plane.

Figure 1:
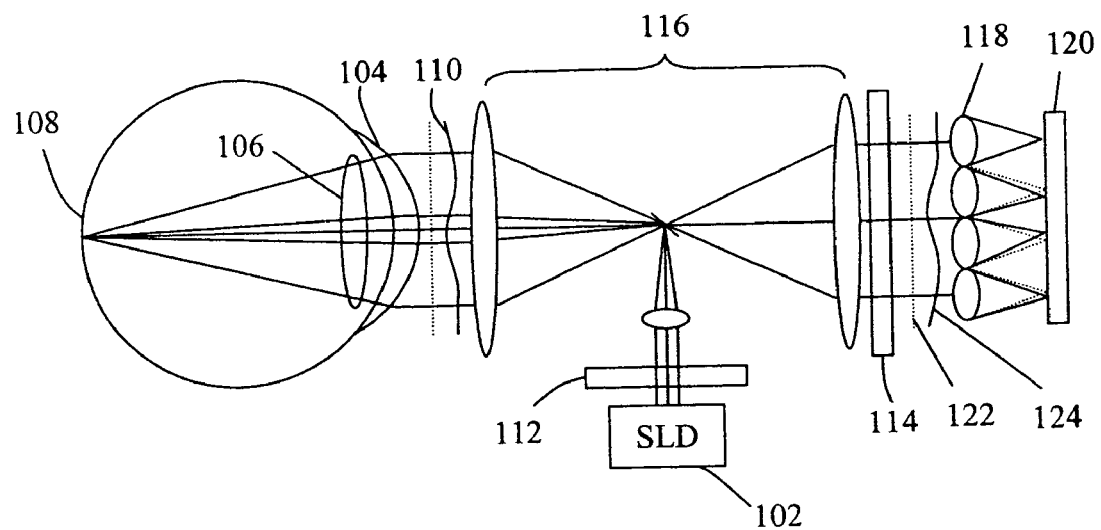
FIG. 1 shows an exemplary prior art Shack-Hartmann sensor used for eye aberration measurement.
Figure 2:
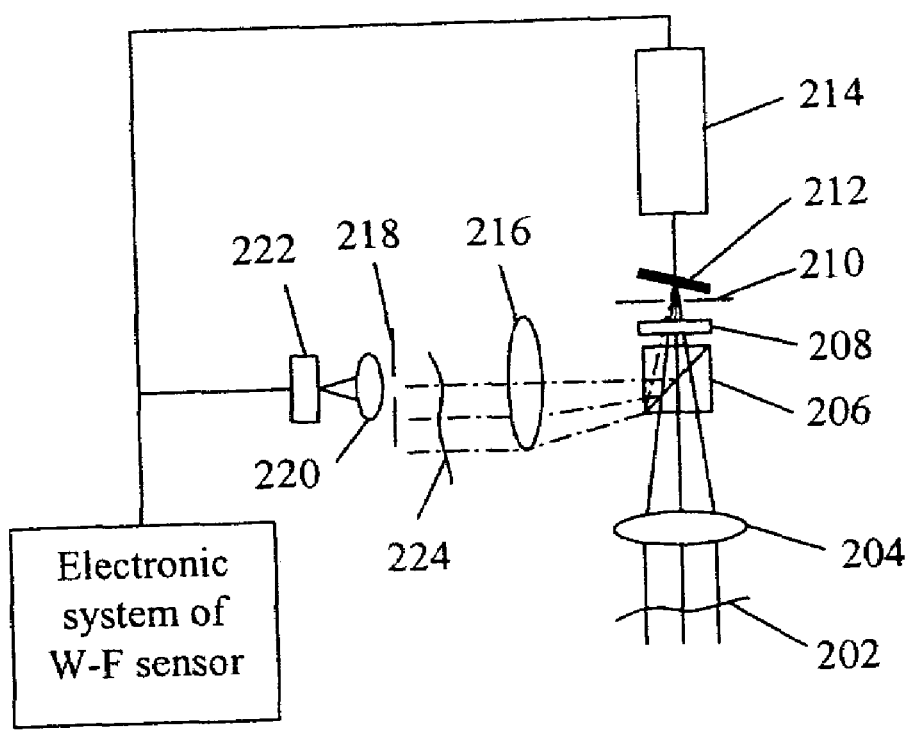
FIG. 2 shows an exemplary schematic diagram of an embodiment of the sequential wavefront sensor.

FIG. 2 shows an exemplary schematic diagram of an embodiment of the sequential wavefront sensor 200. A linearly polarized input beam of light having a wavefront 202 is focused by the first lens 204. The focusing beam travels through a polarization beam splitter (PBS) 206, which is arranged in such a manner that its pass-through polarization direction is aligned with the polarization direction of the incoming beam. As the result, the linearly polarized convergent beam will pass through the PBS 206. A quarter-wave plate 208 is placed behind the PBS 206 with fast axis oriented so that a circularly polarized beam is emerged after passing through the quarter-wave plate 208. A pinhole 210 is placed behind the quarter wave plate 208 and right in front of the scanning mirror 212 to serve the purpose of rejecting the light not directly coming from interested wavefront of the light beam.

The input convergent beam, after passing through the pinhole 210, is focused on the reflective surface of a tilted scanning mirror 212, which is mounted on a motor shaft 214. The light beam reflected by the mirror is divergent, with its beam central chief ray changed to a direction that is dependent on the tilting angle of the scan mirror 212 and the rotational position of the motor 214. It is expected that the reflected beam is still circularly polarized, but the circular polarization rotation direction will be changed from left hand to right hand or from right hand to left hand. Hence, upon passing through the quarter-wave plate 208 for a second time on its return path, the beam becomes linearly polarized again, but with its polarization direction rotated to an orthogonal direction with respect to that of the original incoming beam. Therefore, at the polarization beam splitter 206, the returned beam will be mostly reflected to the left as shown by the dashed light rays in FIG. 2.

A second lens 216 is placed on the left next to the PBS 206 to collimate the reflected divergent beam and to produce a replica of the original input wavefront. Due to the tilting of the scan mirror, the replicated wavefront is transversely shifted. An aperture 218 is placed behind the second lens 216 and right in front of the sub-wavefront focusing lens 220 to select a small portion of the replicated wavefront. The sub-wavefront focusing lens 220 focuses the selected sub-wavefront onto a position sensing device 222, which is used to determine the centroid of the focused light spot generated from the sequentially selected sub-wavefronts. By rotating the motor 214 and changing the tilting angle of the scan mirror 212 in a stepped fashion, the amount of radial and azimuthal shift of the replicated wavefront can be controlled such that any potion of the replicated wavefront can be selected to pass through the aperture 218 in a sequential way. As a result, the overall wavefront of the original incoming beam can be characterized as for the case of a standard Hartmann-Shack wavefront sensor with the exception that the centroid of each sub-wavefront is now obtained in a sequential rather than a parallel manner.

Figure 3:
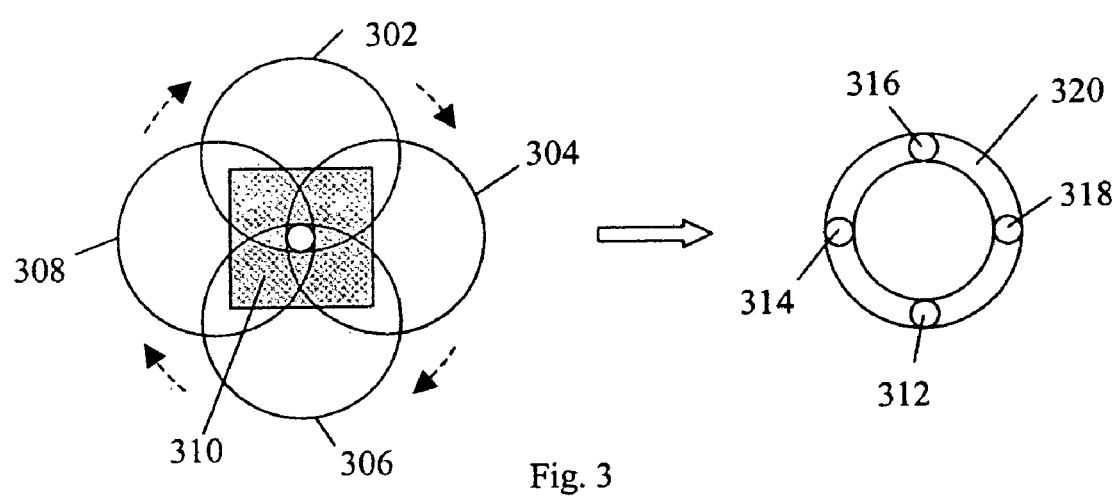
FIG. 3 shows the relative radial and azimuthal shift of a replicated wavefront at 4 symmetrical positions, which corresponds to 4 sub-wavefronts being selected by an aperture around an annular ring of the original wavefront.

In another embodiment, the tilting angle of the scan mirror is fixed and the motor is rotated in multiple steps continuously. As the result, only a selected number of sub-wavefronts around an annular ring of the wavefront will be selected and characterized. This mode of scanning is extremely useful for determining the sphero-cylindrical error or defocus and astigmatism of the original wavefront as discussed in the background section. FIG. 3 shows the radial and azimuthal shift, with respect to the aperture 310, of the replicated wavefronts (302, 304, 306, and 308) at 4 symmetrical stopped motor positions of each revolution, which corresponds to 4 sub-wavefronts (312, 314, 316, 318) being selected by the aperture 310 around an annular ring 320 of the original wavefront.

It is understood that without departing from the scope of the present invention, there can be many variations in terms of components used. For example, quarter wave plate can be a non-zero order quarter wave plate and it can be replaced with a Faraday rotator that can rotate the polarization direction of a returned beam to an orthogonal direction. Meanwhile, the input beam does not have to be linearly polarized and the beam splitter does not need to be restricted to a polarization beam splitter. An ordinary optical beam splitter can be used and in such a case, the quarter-wave plate or Faraday rotator can be removed. Although the optical power efficiency to the detector will be lowered, this may not necessarily affect the performance of the wavefront sensor as long as there is enough optical power delivered to the detector.

The position sensing device (PSD) is a sensor used to measure the centroid of a light spot at various sizes. The position sensing device could be, but not limited to, a quad-detector, PSD sensor or a detector having multiple photosensitive areas such as a small area 2D detector array. Such detectors include the CCD area detector and the CMOS area detector. The lenses used, including 204, 216, 220, do not have to be restricted each to a single lens and can be a combination of lenses as well known to those skilled in the art. The aperture in front of the sub-wavefront focusing lens can be removed if the sub-wavefront focusing lens is as small as a single lenslet. Otherwise, an aperture is preferably needed and the purpose of the aperture is to select a small portion of the wavefront for focusing onto the detector when the sub-wavefront focusing lens used behind the aperture is relatively large. The aperture is not necessarily limited to the configuration of fixed size. A variable size aperture allows selection of sensitivity and resolution during its operation.

Further, the sub-wavefront focusing lens can be replaced with any optical element that can achieve the function of focusing, for example, a graded index lens or a focusing mirror can also be used. Also the number of stops for each revolution of the motor does not need to be limited to 4 and can be any number. Meanwhile, the motor can be rotated continuously and the light source can be short-pulsed to be turned on at different times. The tilting angle of the scan mirror can also be dynamically changed in real time so that different annular ring portions of the wavefront can be selected. In fact, although we used the term "tilted mirror", it should be noted that the term also include the case of zero tilting angle of the mirror, that is, the input beam is normal to the mirror so that the reflected beam is co-axial with respect to the input beam as will direct the central portion of the original wavefront to the detector.

The order of sequence of motor rotation and scanning mirror tilting can also be reversed or mixed so that the selection of sub-wavefronts can be in any desired sequence. Furthermore, the scan mirror and the motor can be replaced, but not limited, by a MEMS (micro-electrical-mechanical-system) mirror, which is currently being brought into the market, or any other deformable mirror as long as it can change the direction of the reflected light beam. The advantage of using a MEMS mirror is that it has a relatively high frequency response because of the low weight of the movable mirror mass, as a result, high speed sequential wavefront sensing can be achieved. In addition, the tilting angle of the MEMS mirror can be easily controlled.

It is understood that without departing from the scope of the present invention, there can also be many variations in terms of system configuration. For example, there is no absolute need to reflect the wavefront backward first and then deflect the beam to the side.

Figure 4:
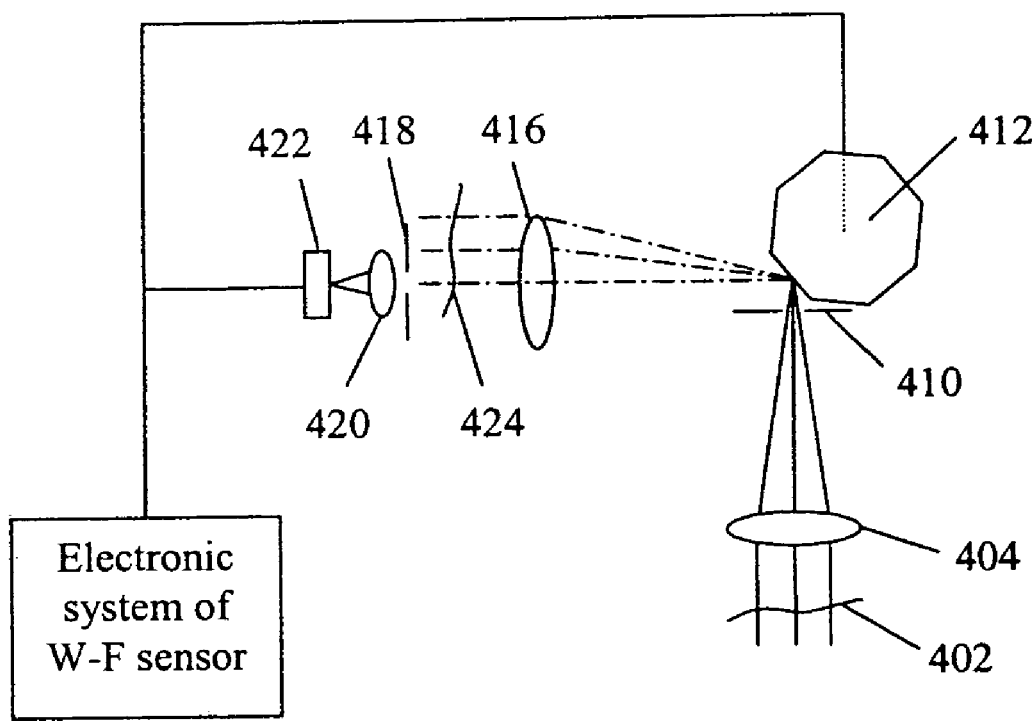
FIG. 4 shows an alternative embodiment of the sequential wavefront sensor, in which the reflected beam is directed sideway by the scan mirror instead of being initially directed backward.

As an alternative, the scan mirror can also be replaced by a non-conventional multiple faceted drum mirror 412 with each reflective surface having a desired spatial orientation such that when each reflective surface is rotated in position in a stepwise or continuous manner, the convergent input beam is reflected with the central chief ray tracing around a cone. FIG. 4 shows a schematic cross sectional view of such a configuration 400, in which the reflected beam is transversally shifted upward. It should be noted that the reflected beam can also be shifted downward, to the left or right, or to any azimuthal direction with any amount of radial displacement. This is because the multiple faceted drum 412 is not a symmetric polygon, when each surface is moved in position to reflect the input convergent beam, it will reflect the beam to a different spatial direction such that a desired portion of the replicated wavefront is selected by the aperture for focusing onto the detector.

Additionally, a pinhole can again be arranged before the multiple faceted mirror along the input light path for rejecting light not coming from the desired direction or location of the input beam. Note that the same configuration can be realized using a MEMS mirror to replace the multiple faceted mirror which will offer all the advantages as mentioned before. Also note that the multiple faceted drum mirror can have such a facet orientation arrangement that when the drum rotates in multiple steps continuously, a number of sub-wavefronts around an annular ring of the wavefront are selected to focus onto the detector.

Figure 5:
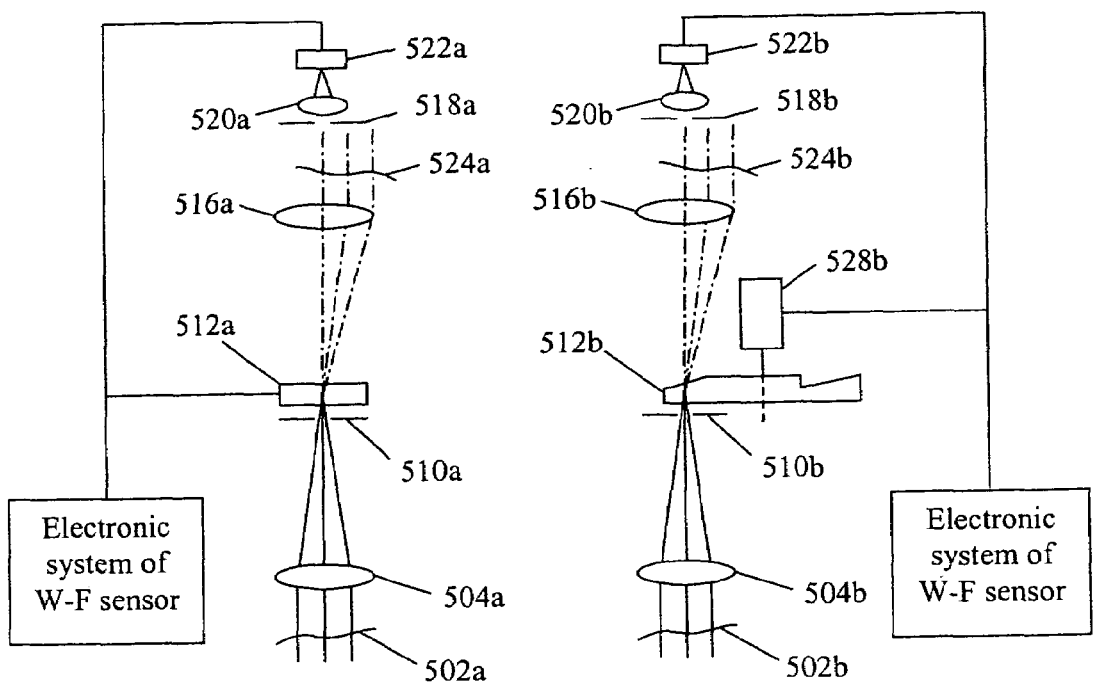
FIG. 5 shows another alternative embodiment of the sequential wavefront sensor, in which a transmissive optical beam scanner is used.

As another alternative, the system can also be configured in a completely transmissive mode instead of a reflective mode. FIG. 5 shows such a configuration in which multiple faceted drum mirror is replaced by transmissive optical beam scanner 512a and 512b. There are a number of different transmissive optical beam scanners commercially available currently, examples include acousto-optic modulator, electro-optic or magneto-optic beam scanner and liquid crystal beam scanner, which are represented by 512a. In such a case, the beam scanner should be able to scan the beam, focused or non-focused dependent on the window side of the transmissive scanner, two-dimensionally in order to sequentially direct a number of desired portions of the wavefront for characterization.

Alternatively, a multiple wedge section disk 512b can also be used for such a purpose. It is understood that, as discussed for the multiple faceted drum mirror in the reflective case, the multiple wedge section disk 512b for the transmissive case should also be a non-symmetric disk in the sense that when one wedge section is rotated in position to deflect the beam focused or non-focused, the wedge angle will determine the emerging beam direction and hence the portion of the wavefront that will be selected by the aperture 518b. Each wedge section should have a different wedge angle orientation to enable a sequence of desired sub-wavefronts to be characterized. Note that if the window of the transmissive scanner is small, the input beam needs to be focused at the location of the transmissive scanner and in such a case, a first lens should be used to focus input optical beam and a second lens should be used to collimate the transmitted beam to produce a replica of the input wavefront that is transversely shifted in space.

Figure 6:
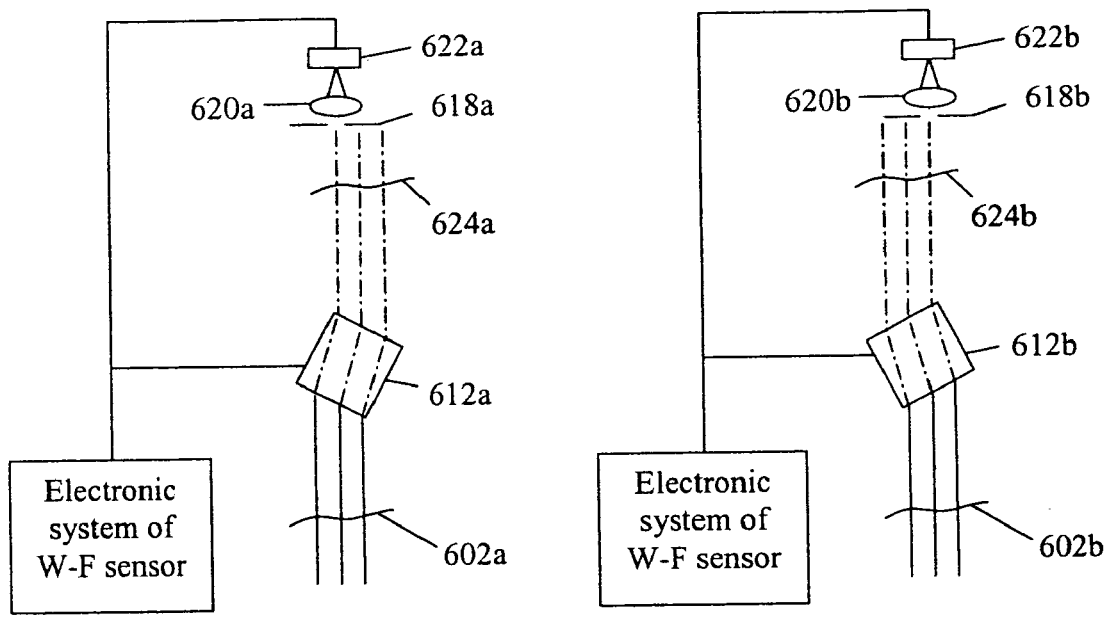
FIG. 6 shows still another alternative embodiment of the sequential wavefront sensor, in which a number of parallel optical blocks of different desired spatial orientation can be switched sequentially into the optical beam path to transversally shift the beam.

In another embodiment of the present invention, the concept of sequentially shifting the input beam wavefront transversely is further extended to include the case of direct transversal shifting of the input beam, in which the input beam is not focused and then re-collimated. Instead, the input beam is directed transversely shifted to direct a desired portion of the wavefront to the aperture (618a, 618b). The advantage of such a scheme is that less optical elements will be needed and hence the light scanning module can be much simplified. FIG. 6 shows such an example in which a number of parallel optical blocks (612a, 612b) of different desired spatial orientation can be switched sequentially into the optical beam path to transversally shift the beam.

Alternatively, the transmissive optical beam scanner can be a multiple faceted transmissive polygon that can be rotated by steps to intercept the optical beam path so as to sequentially transversally shift the beam. Also note that transversal shifting of an optical beam does not necessarily have to be achieved by mechanical means. For example, a liquid crystal cell, an electro-optic cell and a magneto-optic cell can all be used for beam transversal shifting purpose, in which case, the change in the effective refractive index of the cell will change the amount of transversal beam shift. As in the case of the reflective optical beam scanner, the transmissive optical beam scanner can be made to enable a number of sub-wavefronts around an annular ring of the wavefront to be selected to focus onto the detector for defocus and astigmatism aberration sensing.

The above-described wavefront sensor can be used for a large number of applications. A first major application is in adaptive optics in which the measured distorted wavefront can be compensated in real time using a wavefront compensation device such as a deformable mirror array. In such a case, the speed for scanning the beam needs to be relative high and therefore high speed beam scanners or shifters such as MEMS mirror and electro-optic or magneto-optic cells should preferably be used.

A second major application of the above-described embodiments is in autofocusing and/or astigmatism correction. Due to the fact that only a small number (for example, 8) of sub-wavefronts around an annular ring need to be characterized in order to deduce the defocus and astigmatism of an imaging system such as that of a human eye, the optical beam scanning module does not need to have very high frequency response and accordingly, low cost beam scanners such as a tilted mirror mount on a step motor as shown in FIG. 4 will be sufficient. For example, the above-described wavefront sensor can be used in a fundus camera for real time defocus and/or astigmatism correction of an eye imaging system as described in U.S. Pat. Nos. 6,361,167 and 6,685,317 so that a high resolution fundus image can be obtained.

Another feature of the above-described wavefront sensor is that when it is applied to the characterization of only defocus and/or astigmatism, a quad-detector will be sufficient and its output can be processed to produce a sequential trace or pattern that can be displayed on a monitor to indicate in real time, whether the optical imaging system in front of the wavefront sensor is in focus or not, how far off the focus is, whether the defocus is convergent or divergent, the amount of astigmatism, as well as the axis of astigmatism.

Figure 7:
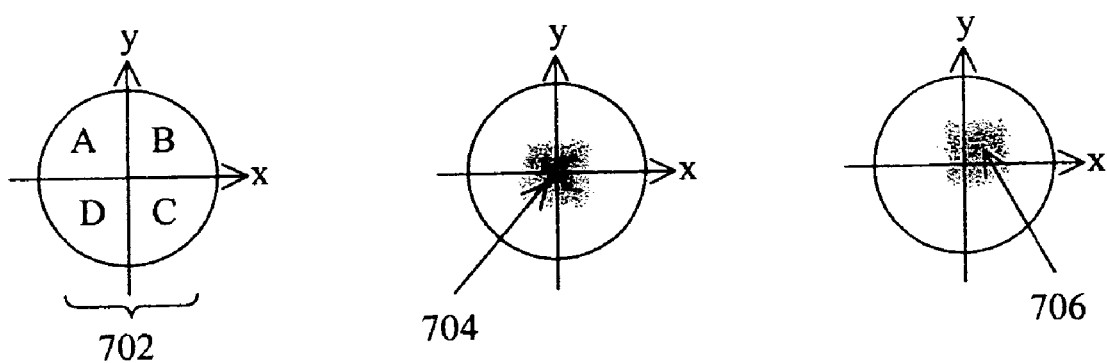
FIG. 7 shows a quad-detector with four photosensitive areas of A, B, C, and D, and the image spot on the quad-detector for a normal incident sub-wavefront and a non-normal incident wavefront.

Assume a quad-detector 702 with four photosensitive areas of A, B, C, and D as shown in FIG. 7. If the sub-wavefront is incident at a normal angle with respect to the sub-wavefront focusing lens in front of the quad-detector, the image spot 704 on the quad-detector will be at the center and the four photosensitive areas will receive the same amount of light, with each area producing a signal of the same strength. On the other hand, if the sub-wavefront departs from normal incidence with a tilting angle (say, pointing toward the right-upper direction), the image spot on the quad-detector will then be formed away from the center (moved towards the right-upper quadrant as shown by the image spot 706). The departure (x, y) of the centroid from the center (x=0, y=0) can be characterized using the following equation:

$$x = \frac{(B+C)-(A+D)}{A+B+C+D} \quad (1)$$
$$y = \frac{(A+B)-(C+D)}{A+B+C+D}$$

where A, B, C and D stand for the signal strength of each corresponding photosensitive area of the quad-detector and the denominator (A+B+C+D) is used to normalize the measurement so that the effect of optical source intensity fluctuation can be cancelled.

When a number of symmetric sub-wavefronts (for example, 4, 8 or 16) around an annular ring of an optical beam is sequentially projected (for example, in a clockwise direction) onto the sub-wavefront focusing lens and quad-detector, the departure of the centroid as indicated by (x, y) of Equation (1) from the center of the quad-detector will trace a pattern on an x-y plane that can be displayed on a monitor and also be processed digitally to represent the status of defocus and astigmatism.

Figure 8:
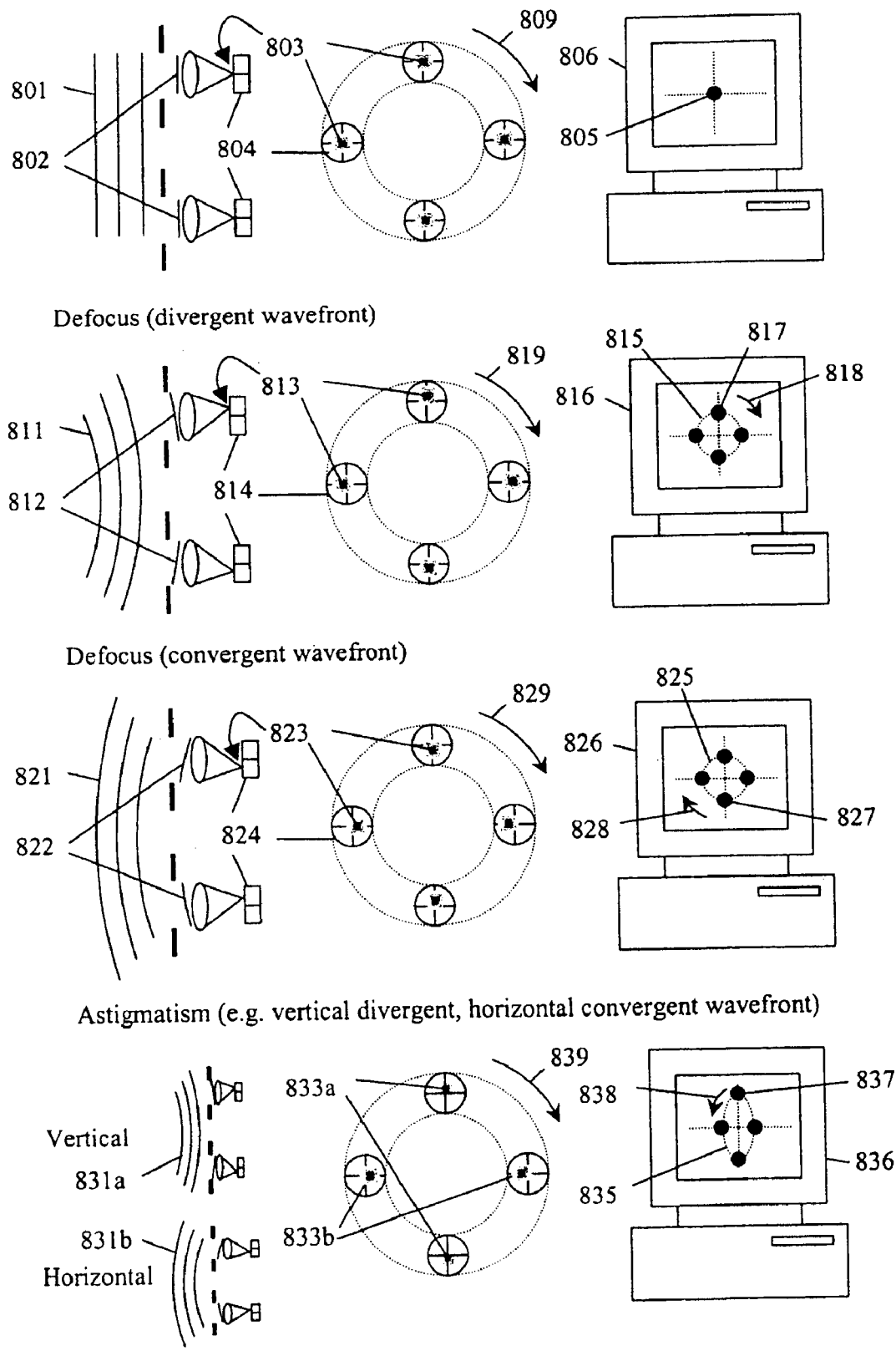
FIG. 8 shows a number of representative cases of well in-focus, defocus and astigmatism, the associated image spot pattern on the quad-detector behind a sub-wavefront focusing lens, as well as the sequential movement of the corresponding centroid positions when displayed on a monitor.

FIG. 8 shows a number of representative cases of well in-focus, defocus and astigmatism, the associated image spot pattern on the quad-detector behind the sub-wavefront focusing lens, as well as the sequential movement of the corresponding centroid positions when displayed on a monitor. Note that instead of drawing a number of wavefronts being projected with different sub-wavefronts onto the same sub-wavefront focusing lens and quad-detector, we have taken the equivalent representation as shown in FIG. 3 in which a number of sub-wavefronts are drawn around the same annular ring and accordingly, a number of quad-detectors are drawn around the same annular ring to represent the case of scanning different portions of a wavefront to a sub-wavefront focusing lens and a single quad-detector.

Assume that we start the scan around the wavefront annular ring from the top sub-wavefront and move in a clockwise direction to the second sub-wavefront on the right and so forth as indicated by the arrow 809. It can be seen from FIG. 8 that when the wavefront is a plane wave 801 which means that the optical system is well in focus without any aberration, all the sub-wavefronts (for example, 802) will form an image spot 803 at the center of the quad-detector 804 and as a result, the centroid trace 805 on a monitor 806 will also be always at the center of the x-y plane. Therefore, an all at the x-y plane center centroid pattern or trace can be used to indicate the status of well in-focus.

However, for a more general case, there may always be some aberration of the input wavefront that will move some the centroid away from the x-y plane center, such as the case of astigmatism as will be discussed shortly. Hence, with the presence of other aberrations, minimizing the scattering of the centroids from the x-y plane center can be used as a criteria for autofocusing or assisted focusing. In such a case, the scattering of the centroids can be defined as a summation of the absolute distance of each centroid from a common center and this signal can be used as a feedback signal in a closed-loop control system for autofocusing.

When the input wavefront is divergent as shown by 811, the center of the image spot 813 of each sub-wavefront 812 will be on the radially outward side from the wavefront center with an equal amount of departure from the center of the quad-detector 814, and as a result, the trace 815 on the monitor 816 will be a clockwise circle as indicated by the arrow 818 starting from the top position 817. If, on the other hand, the input wavefront is convergent as shown by 821, the center of the image spot 823 of each sub-wavefront 822 will be on the radially inward side relative to the center of the wavefront with an equal amount of departure from the center of the quad-detector 824, as a result, the centroid trace 825 on the monitor 826 will still be a circle but will start from the bottom position 827 and will still be clockwise as indicated by the arrow 828. Hence when a sign change for both the x-axis centroid position and the y-axis centroid position is detected, it is an indication that the input wavefront is changing from a divergent beam to a convergent beam or the other way round. Furthermore, the starting point of the centroid trace can also be used as a criteria to indicate if the input wavefront is divergent or convergent.

This sign change or starting point change criteria can hence be used as a feedback to indicate if the optical system in front of the wavefront sensor is well in focus or not. In practice, there may be other wavefront aberrations present and hence a sign change for all the centroid position may not happen at the same time. A preferred practice could be to define a critical amount of focus adjustment in the optical system in front of the wavefront sensor such that if the within the preset focus adjustment range, all or most of the centroid signs have changed, then the wavefront can be considered as in focus. In one embodiment of the present invention, this sign change can hence be used as a criteria for autofocusing or assisted focusing, in which, a high speed focus adjustment optical element or module such as a movable lens axially driven in a closed-loop control fashion by a high speed motor can be arranged in the optical system in front of the wavefront sensor to maintain the optical system always in focus by locking the system at the sign change point. Alternatively, other types of focus adjustable lenses such as a liquid surface tension lens, a liquid crystal lens or an acousto-optic lens can also be used for the same purpose.

For the case of both a divergent and a convergent spherical input wavefront, the rotation direction of the sequential centroid trace on the x-y plane is the same as the scanning direction of the sub-wavefronts around the annular ring of the input wavefront. In this embodiment of the invention, we define this same rotation direction as normal. As will be discussed shortly, for the case of an astigmatic input wavefront, it can happen that the rotation direction of the sequential centroid trace on the x-y plane is the opposite when compared to the scanning direction of the sub-wavefronts around the annular ring of the input wavefront, we define this opposite rotation direction as abnormal.

Figure 9:
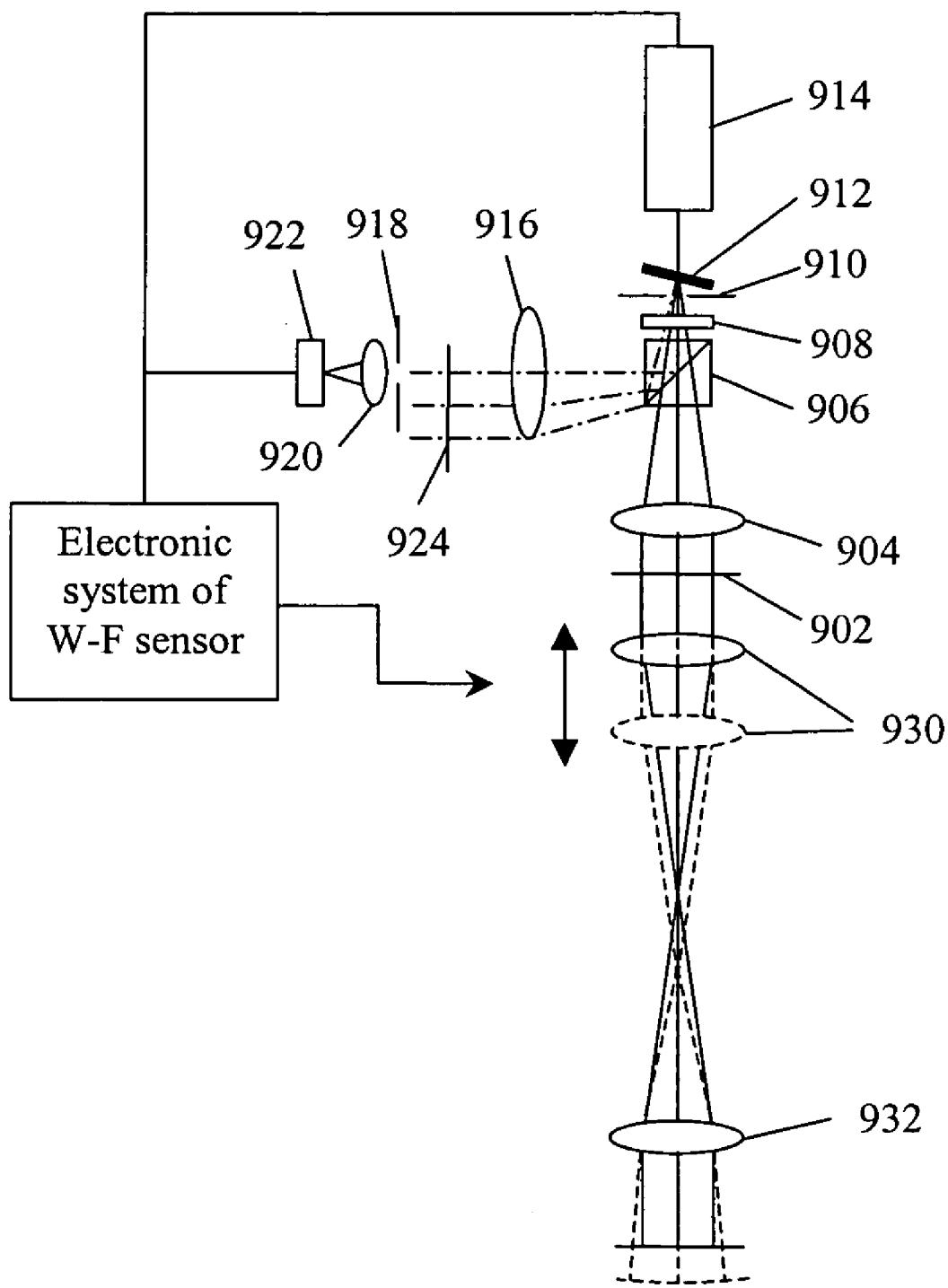
FIG. 9 depicts a system in which a high speed focus adjustment optical element or module is driven in a closed-loop control fashion by a high speed motor to maintain the optical system in focus.

For the cases of normal centroid trace rotation on the x-y plane, if the trace is circular, the diameter of circular trace (815, 825) can obviously be used to indicate the degree of defocus. In practice, as there may always be some other aberrations and hence the centroid trace may not be perfectly circular, a good practice might be to fit the centroid trace to a circle and then to derive an averaged diameter or radius of the trace. In one embodiment of the present invention, the criteria of achieving a minimum averaged diameter or radius of a centroid trace is used for assisted focusing or autofocusing, in which, a high speed focus adjustment optical element or module such as a movable lens (930) axially driven in a closed-loop control fashion by a high speed motor can be arranged in the optical system in front of the wave front sensor to maintain the optical system always in focus as shown in FIG. 9. Alternatively, a focus adjustable lens such as a liquid surface tension lens, a liquid crystal lens or an acousto-optic lens can also be used for the same purpose.

It can also be seen from FIG. 8 that when the input wavefront is astigmatic, it can happen that when the input wavefront is roughly in focus, the wavefront can be divergent in the vertical direction as shown by 831*a* and convergent in the horizontal direction as shown by 831*b*, as a result, the centroid position of the vertical sub-wavefronts 833*a* will be located radially outward with respect to the center of the input wavefront, and the centroid position of the horizontal sub-wavefronts 833*b* will be located radially inward with respect to the center of the input wavefront. Consequently, the centroid trace 835 on the monitor 836 will start from the top position 837 but move anti-clockwise as indicated by arrow 838, hence the centroid trace rotation is now abnormal. Note that when we say that the astigmatic wavefront is roughly in focus, we mean that along one axis of the astigmatic wavefront, the sub-wavefronts are divergent, and along the other axis of the astigmatic wavefront, the sub-wavefronts are convergent. In one embodiment of the present invention, this abnormal rotation direction of the centroid trace can be used to first indicate that the input wavefront is astigmatic and second to indicate that the astigmatic wavefront is roughly in focus. The circularity of the abnormal centroid trace can also be used to indicate is the astigmatic input wavefront is in relatively well focus or not.

On the other hand, if the input wavefront is astigmatic but all the sub-wavefronts are either entirely divergent or entirely convergent, the rotation of the centroid trace will be clockwise (i.e. normal) based on a similar argument as has been done for the divergent and convergent defocused wavefront, however, for the astigmatic case, the trace of the centroid on the monitor will be elliptic rather than circular since the sub-wavefronts along one astigmatic axis will be more divergent or convergent than those along the other axis. For a more general astigmatic wavefront, either the centroid trace will rotate in an abnormal direction with the trace either elliptical or circular, or the centroid trace will rotate in the normal rotation direction but the trace will be elliptical. The axis of the ellipse can be in any radial direction relative to the center of the wavefront, which will indicate the axis of the astigmatism. In such a case, 4 sub-wavefronts around an annular ring may not be enough and more sub-wavefronts (such as 8 or 16 instead of 4) can be projected onto the sub-wavefront focusing lens and the quad-detector and be characterized.

Figure 10:
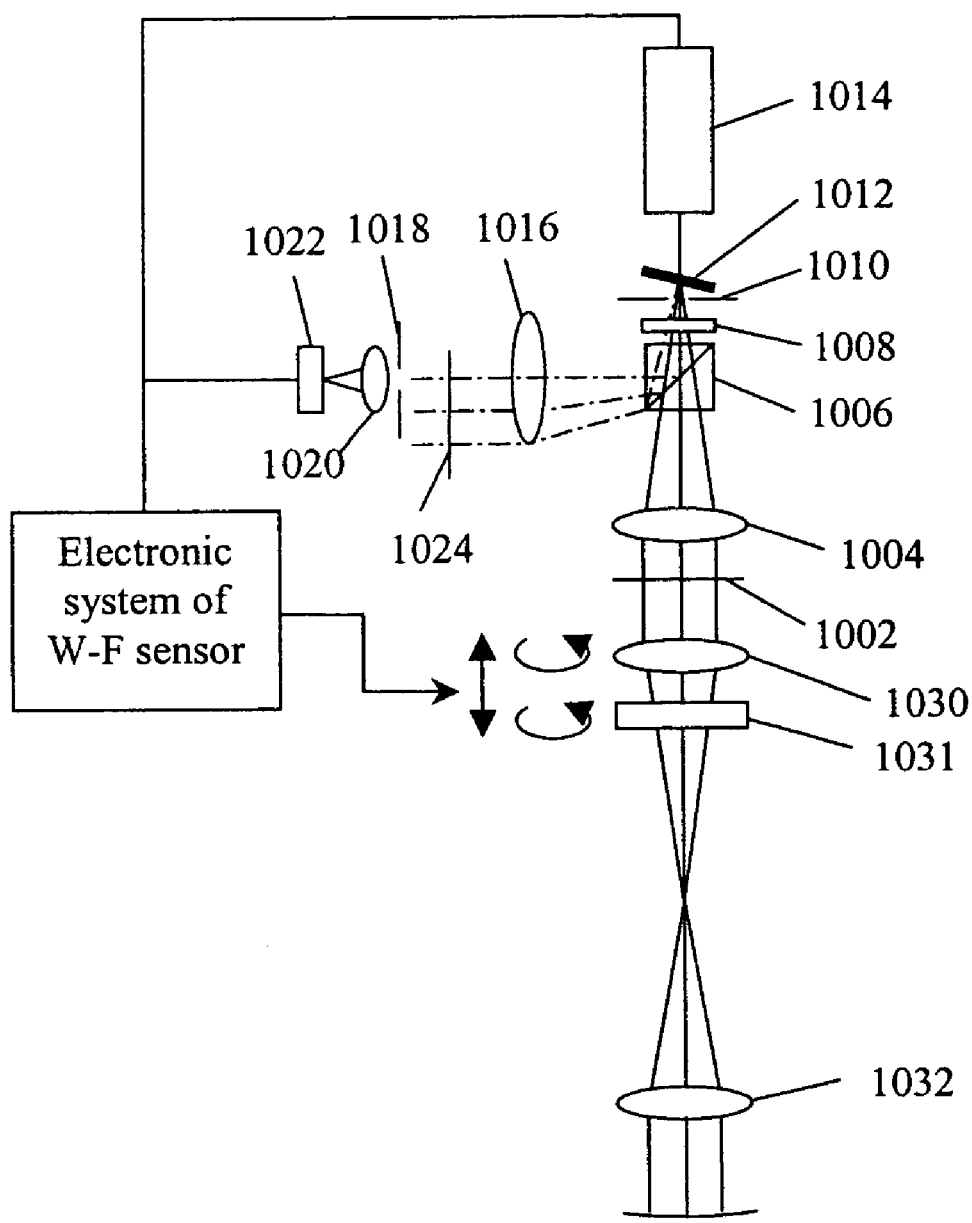
FIG. 10 depicts a system in which the rotation condition of the centroid trace can be used as a feedback in a closed-loop control system to rotate two cylindrical lenses to control and correct astigmatism.

In one embodiment of the present invention, the ellipticity of a normal centroid trace or the relative difference in the length of the two elliptical axes is used to indicate the degree of astigmatism. In another embodiment of the present invention, the axis of a normal elliptic centroid trace is used to indicate the axis of astigmatism. In still another embodiment of the present invention, the wave front sensor can be used to provide a feedback signal to correct for the astigmatism of the optical system in front of the wavefront sensor module. In such a case, the rotation direction, the elliptic axis and the ellipticity of the centroid trace can all be used as a feedback in a closed-loop control system to activate an astigmatism correction element, such as to rotate, as a combined element, two cylindrical lenses 1030, 1031 (as shown in FIG. 10). In such a case, if the centroid trace rotation is normal, the ellipticity of the centroid trace can be minimized and hence the circularity of the trace is maximized to achieve auto-astigmatism-correction. On the other hand, if the centroid trace rotation is abnormal, a good criteria to correct for the astigmatism is to firstly shorten one of the two elliptic trace axes to turn the centroid trace to normal rotation and then to lengthen the same axis to circularize the centroid trace. As a result, auto-astigmatism-correction can also be achieved.

In another embodiment of the present invention, the auto-focusing mode of operation is combined with the auto-astigmatism-correction mode of operation, so that a real time correction of both defocus and astigmatism for an optical imaging system such the human eye can thus be achieved. A preferred practice would be to achieve astigmatism correction first and then correct for defocus. However, this does not mean that the sequence cannot be reversed, in fact, an iterative process can be used to switch between the two corrections until a certain criteria is reached. As discussed in the background section of this application, defocus and astigmatism are the two major aberrations that can substantial affect the quality of an optical imaging system. Therefore, by correcting these two major aberrations using the above-described wavefront sensor, a high quality image such as a fundus image of a human eye can be obtained.

Although in the above discussions on characterizing and correcting for defocus and astigmatism, we have used a quad-detector to illustrate the principle of operation, other detectors can also be used as long as they can provide the information of the centroid positions. We have previously mentioned that the detector can be an area CCD or an area CMOS detector array. Obviously, these detectors can also be used in place of the quad-detector for characterizing and correcting for defocus and astigmatism as discussed above.

The presently above-described sensor can have many other applications in addition to being used as an advanced sensor in a fundus camera for auto-focusing and astigmatism correction. For example, it can be used in an optical alignment tool, the core technology can also be used for as the bases of a new auto-refractor. The sensor can also be used as a general focusing sensor in any application.

The invention may be implemented, in part, as program code, stored on a computer readable medium, that is executed by a digital computer. The computer readable medium may include, among other things, magnetic media, optical media, electro-magnetic fields encoding digital information, and so on.

It is understood that the description of the preferred embodiments of the invention are only for illustration purpose. Those skilled in the art may recognize other equivalent embodiments to those described herein; which equivalents are intended to be encompassed by the claims attached hereto. For example, the descriptions are for the case in which a single sub-wavefront focusing lens and a single quad-detector are used, however, this does not mean that the same principle of scanning a wavefront to project different positions of a wavefront cannot be applied to the case of two or more quad-detectors or other detection modules. The light scanning module can also project a multiple number of portions of the input wavefront onto a number of detection modules to further shorten the time for completing a series of sub-wavefront characterization. For example, the principle can be extended to the case in which a linear array of lenslets are arranged parallel to a linear array of quad-detectors and as a result, the sequential scanning of the input wavefront can be achieved by scanning the wavefront in a direction that is perpendicular to the linear array of lenslets and quad-detectors.

What is claimed is:

1. A sequential wavefront sensor comprising:
   a wavefront scanning device adapted to sequentially shift an incident wavefront by a first displacement in a first dimension and a second displacement in a second dimension
   an aperture positioned to intercept and configured to select a portion of the incident wavefront shifted by the sequential scanning device;
   a focusing element configured to focus the portion of the shifted incident wavefront selected by the aperture onto a position sensing device; and
   with the position sensing device configured to indicate the two-dimensional displacement from a reference point of the portion of the shifted incident wavefront focused by the focusing element onto the position sensing device.

2. The sequential wavefront sensor of claim 1 where the wavefront scanning device further comprises:
   a wavefront scanner for sequentially shifting the incident wavefront in a transverse direction.

3. The sequential wavefront sensor of claim 2 where the wavefront scanner comprises:
   an electric motor having a shaft; and
   a tilted mirror located on the shaft.

4. The sequential wavefront sensor of claim 3 wherein:
   the motor is a stepper motor and the tilted mirror is mounted at a fixed angle on the end of the shaft so that a number of sub-wavefronts around an annular ring of the incident wavefront are selected when the shaft is rotated.

5. The sequential wavefront sensor of claim 2 where the wavefront scanner comprises:
   an electric motor having a shaft; and
   an asymmetric multiple-faceted drum mirror mounted on the shaft.

6. The sequential wavefront sensor of claim 1 wherein the position sensing device is a quad detector having four photo-sensitive areas.

7. The sequential wavefront sensor of claim 2 where the wavefront scanner comprises:
   a MEMS-based scanner.

8. The sequential wavefront sensor of claim 2 where the wavefront scanner comprises:
   a transmissive optical beam scanner.

9. The sequential wavefront sensor of claim 1 wherein:
   the aperture is a variable aperture for controlling the size of the portions of the selected incident wavefront.

10. A method for detecting aberration of an incident wavefront, said method comprising:
    sequentially shifting an incident wavefront by a first displacement in a first dimension and a second displacement in a second dimension
    intercepting and selecting a portion of a shifted incident wavefront with an aperture;
    focusing the portion of the shifted incident wavefront selected by the aperture onto a position sensing device; and
    determining the two-dimensional deflection of the portion of the incident wavefront focused on the position sensing device from a reference point on the position sensing device.

11. The method of claim 10 further comprising:
    analyzing a plurality of two-dimensional deflections to characterize the aberration of the incident wavefront.

12. The method of claim 11 where the position sensing device is a quad detector having a reference point and said step of determining the deflection further comprises:
    calculating two-dimensional deflection coordinates of the portion of the incident wavefront focused on the quad detector.

13. The method of claim 12 where selecting further comprises:
    sequentially selecting a portion of a shifted incident wavefront disposed around an annular ring of the incident wavefront, and where analyzing further comprises:
    determining the scattering of the two-dimensional deflections.

14. The method of claim 12 where selecting further comprises:
    sequentially selecting a portion of the shifted incident wavefront disposed around an annular ring of the incident wavefront; and where analyzing further comprises:
    detecting a sign change in the location of a focused portion to indicate a change of the input waveform between a convergent waveform and a divergent waveform.

15. The method of claim 10 further comprising:
    pulsing or bursting a light source that generates the wavefront.

16. The method of claim 11 further comprising:
    displaying the two-dimensional deflections to form a pattern on a display device.

17. The method of claim 12 where the position sensing device is a quad detector having a reference point and where displaying the deflections further comprises:
    displaying each focused portion based on its calculated coordinates.

18. The method of claim 14 further comprising:
    displaying two-dimensional deflections on a display device in real time.

19. A method for compensating aberrations of an incident wavefront, said method comprising:
    sequentially shifting an incident wavefront by a first displacement in a first dimension and a second displacement in a second dimension;

intercepting and selecting a portion of the shifted incident wavefront with an aperture;

focusing the portion of the shifted incident wavefront selected by the aperture onto a position sensing device;

measuring the two-dimensional deflection of the focused portion of the shifted incident wavefront focused onto the position sensing device from a reference point on the position sensing device to determine the aberration of the incident wavefront; and forming a feedback criteria based on the two-dimensional deflection of the focused portion of the shifted incident wavefront.

20. The method of claim 19 further comprising:

controlling an optical wavefront compensation device with the feedback criteria to compensate aberration of the incident wavefront.

21. The method of claim 19 where selecting further comprises:

sequentially selecting a number of portions of the shifted incident wavefront around an annular ring of the incident wavefront.

22. The method of claim 21 further comprising:

displaying the two-dimensional deflections on a display device in real time.

23. The method of claim 21 where said step of forming a feedback criteria further comprises:

minimizing the scattering of the deflections as a criteria to correct defocus of the wavefront.

24. The method of claim 21 where said step of forming a feedback criteria further comprises:

detecting a sign change of the deflection of a focused portion as a criteria to indicate when an optical system in front of the wavefront is in focus.

25. The method of claim 21 where said step of forming a feedback criteria further comprises:

detecting the deviation of a deflection-formed pattern from a circle as a feedback criteria to correct astigmatism of the wavefront.

26. The method of claim 21 where said step of forming a feedback criteria further comprises:

detecting abnormal rotation of a deflection-formed pattern as a feedback criteria for correcting an astigmatic wavefront.

27. The method of claim 21 where said step of forming a feedback criteria further comprises:

detecting ellipticity of the deflection-formed pattern as a feedback criteria for correcting astigmatism.

28. A wavefront compensation system comprising:

a wavefront scanning device adapted to sequentially shift an incident wavefront by a first displacement in a first dimension and a second displacement in a second dimension an aperture positioned to intercept and configured to select a portion the incident wavefront shifted by the sequential scanning device;

a focusing element configured to focus the portion of the shifted incident wavefront selected by the aperture onto a position sensing device;

with the position sensing device configured to indicate the two-dimensional displacement from a reference point of the portion of the shifted incident wavefront focused by the focusing element onto the position sensing device;

a wavefront aberration analyzing device that generates a feedback signal based on detected locations of the sequentially selected portions of the shifted incident wavefront; and a wavefront compensation device for compensating aberrations in the wavefront that utilizes the feedback signal in a closed loop control system to activate compensation.

29. The system of claim 28 with the wavefront compensation device comprising:

an axially driven optical lens for focusing the wavefront.

30. The system of claim 28 with the wavefront compensation device comprising:

an rotationally driven astigmatism correction element.

31. A sequential wavefront sensor comprising:

a wavefront scanning device adapted to sequentially shift an incident wavefront so that an annular ring is sampled;

an aperture positioned to intercept and configured to select a portion the incident wavefront shifted by the wavefront scanning device;

a focusing element configured to focus the portion of the shifted incident wavefront selected by the aperture onto a position sensing device; and with the position sensing device configured to indicate the two-dimensional displacement from a reference point of the portion of the shifted incident wavefront focused by the focusing element onto the position sensing device.

32. A sequential wavefront sensor comprising:

a wavefront scanning device adapted to sequentially shift an incident wavefront by a first displacement in a first dimension and a second displacement in a second dimension;

a variable aperture positioned to intercept and configured to select a portion the incident wavefront shifted by the wavefront scanning device, with the size of the aperture being variable so that the sensitivity and resolution can be controlled;

a focusing element configured to focus the portion of the shifted incident wavefront selected by the aperture onto a position sensing device; and with the position sensing device configured to indicate the two-dimensional displacement from a reference point of the portion of the shifted incident wavefront focused by the focusing element onto the position sensing device.

33. A system comprising:

a position sensing device configured to indicate the two-dimensional displacement of an incident image spot;

an aperture configured to pass through a portion of a wavefront to project an image spot onto the position sensing device; and a scanning device configured to sequentially direct any portion of an incident wavefront to pass through the aperture.

34. The system of claim 33 where the scanning device comprises:

a reflective element configured to be stepped in arbitrary radial and azimuthal directions.

35. The system of claim 33 where the scanning device comprises:

a reflective element configured to continually shift the incident wavefront in arbitrary radial and azimuthal directions.

36. An apparatus comprising:

an aperture disposed along an aperture plane;

an optical system configured to replicate an incident wavefront onto the aperture plane, a wavefront positioning device, included in the optical system, configured to project the incident wavefront with a selected two-dimensional transversal displacement onto the aperture plane so that any portion of the projected replicate of the incident wavefront can be selected to pass through the aperture;

a focusing element configured to focus the portion of the projected replicate of the incident wavefront selected to pass through the aperture onto a position sensing device; and with the position sensing device configured to indicate the two-dimensional displacement from a reference point of the portion of the incident wavefront focused by the focusing element onto the position sensing device.

* * * * *